United States Patent [19]

Papenfuhs et al.

[11] Patent Number: 5,200,556
[45] Date of Patent: Apr. 6, 1993

[54] PROCESS FOR THE PREPARATION OF 3,4,6-TRIFLUOROPHTHALIC ACID AND THE ANHYDRIDE THEREOF

[75] Inventors: Theodor Papenfuhs, Frankfurt am Main; Ralf Pfirmann, Griesheim, both of Fed. Rep. of Germany

[73] Assignee: Hoechst Aktiengesellschaft, Frankfurt am Main, Fed. Rep. of Germany

[21] Appl. No.: 887,182

[22] Filed: May 21, 1992

[30] Foreign Application Priority Data

May 22, 1991 [DE] Fed. Rep. of Germany ....... 4116625

[51] Int. Cl.$^5$ .................... C07D 307/89; C07C 51/06
[52] U.S. Cl. .................................. 562/480; 549/246; 562/483
[58] Field of Search ................ 549/246; 562/483, 480

[56] References Cited

U.S. PATENT DOCUMENTS

| | | | |
|---|---|---|---|
| 1,935,648 | 11/1933 | Mares | 549/246 |
| 2,460,564 | 2/1949 | Amacker | 549/246 |
| 3,007,943 | 11/1961 | Hoffmann | 549/246 |
| 3,092,641 | 6/1963 | Leon | 549/246 |
| 3,240,792 | 3/1966 | Patrick et al. | 549/246 |
| 4,302,396 | 11/1981 | Tsujimoto et al. | 549/246 |
| 4,814,467 | 3/1987 | Bay et al. | 549/246 |
| 4,962,206 | 10/1990 | Coceman et al. | 569/246 |
| 5,086,188 | 2/1992 | Fertel et al. | 562/480 |

FOREIGN PATENT DOCUMENTS

| | | | |
|---|---|---|---|
| 170190 | 2/1986 | European Pat. Off. | 549/246 |
| 1518647 | 2/1969 | Fed. Rep. of Germany | 549/246 |
| 2814947 | 10/1978 | Fed. Rep. of Germany | 549/246 |
| 1-160944 | 6/1989 | Japan . | |
| 2306945 | 12/1990 | Japan | 549/246 |
| 958294 | 5/1964 | United Kingdom | 549/246 |

OTHER PUBLICATIONS

Hashem, J. Appl. Chem. Biotechnol (1972) 22, 1041–1042.
Delbridge, T. G., *Am. Chem. J.* 41:393, 400–409 (1909).
O'Reilly, N. J., et al. *Synlet*:339–340, Jun. 1990.
O'Reilly, N. J., et al, *Synlet*:609–610, Oct. 1990.

*Primary Examiner*—Cecilia Tsang

[57] ABSTRACT

Process for the preparation of 3,4,6-tetrafluorophthalic acid of the formula (1)

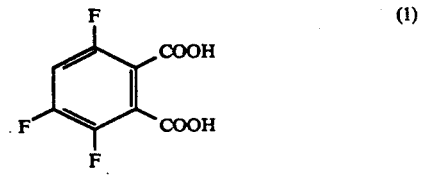

or the anhydride thereof in good yields and in an advantageous manner, by dehalogenating tetrafluorophthalic anhydride of the formula (2)

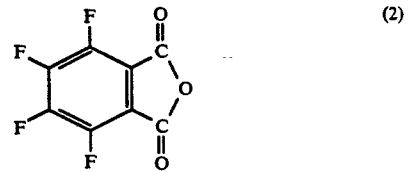

or tetrafluorophthalic acid in aqueous-alkaline medium using zinc at temperatures of approximately 20° C. to approximately 160° C. and, if appropriate, converting the resulting 3,4,6-trifluorophthalic acid into the anhydride in a known manner by dehydrating it.

8 Claims, No Drawings

PROCESS FOR THE PREPARATION OF 3,4,6-TRIFLUOROPHTHALIC ACID AND THE ANHYDRIDE THEREOF

The present invention relates to an improved process for the preparation of 3,4,6-trifluorophthalic acid or the anhydride thereof, which are valuable intermediates for the preparation of potent antibacterial agents. For example, 3,4,6-trifluorophthalic acid can be converted into 2,4,5-trifluorobenzoic acid by various methods by means of decarboxylation (U.S. Pat. No. 4,935,541, Occidental Chem. Corp., 19.6.90; JP 01,160,944, Nippon Carbide Industries Co., Inc., 23.6.89; JP 01,052,737, Nippon Carbide Industries Co., Inc., 28.2.89; JP 01,025,737, Nippon Carbide Industries Co., Inc., 27.1.89), which, in turn, can be reacted by processes known from the literature (PCT Int. Appln. WO 8906649, Warner-Lambert Co., 27.7.89; J. Med. Chem. 31 (5), 983–991 (1988), Warner-Lambert Co.; EP 227,088, Abbott Laboratories, 1.7.87; EP 164,619, Bayer AG, 12.10.88; DE 3,600,891, Bayer AG, 16.7.87; DE 3,420,743, Bayer AG, 5.12.85; EP 191,185, Daiichi Seiyaku Co., Ltd., 20.8.86; JP 60,072,885, Daiichi Seiyaku Co., Ltd., 20.4.85) to give quinolonecarboxylic acid derivatives. Apart from 2,3,4,5-tetrafluorobenzoic acid, 2,4,5-trifluorobenzoic acid is the most important raw material for the preparation of such antibacterial agents.

It is known to prepare 3,4,6-trifluorophthalic acid by reductive dehalogenation of 3,4,5,6-tetrafluorophthalodinitrile in acid solution by means of metallic zinc (JP 01,160,944,A2; Nippon Carbide Industries Co., Inc., 23.6.89). However, the industrial feasibility of this process is limited by problems with materials caused by corrosion due to hydrogen fluoride. Furthermore, the use of zinc in acid solution at increased temperatures leads to rapid evolution of hydrogen which, on the one hand, causes safety problems and, on the other hand, means that larger amounts of zinc are required for the dehalogenation.

Moreover, 3,4,6-trifluorophthalic acid can be prepared by acid hydrolysis of N-alkyl- or aryltrifluorophthalimides (N. J. O'Reilly, W. S. Derwin, L. B. Fertel, H. C. Lin, Synlett (1990), 609–610) which, in turn, can be obtained from the corresponding trichloro compounds by halex reaction. The hydrolysis liberates the alkyl- or arylammonium compounds which must be either recovered or eliminated from the waste water by purification. The process according to the invention avoids these disadvantages. The additional advantage of the process according to the invention for the preparation of 3,4,6-trifluorophthalic acid compared with the known processes is that tetrafluorophthalic anhydride can be used as a starting compound.

It has now been found that 3,4,6-trifluorophthalic acid of the formula (1)

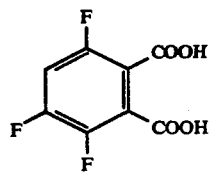

or the anhydride thereof can be prepared in good yields and in an advantageous manner by dehalogenating tetrafluorophthalic anhydride of the formula (2)

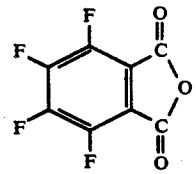

or tetrafluorophthalic acid using zinc, preferably zinc dust, in aqueous-alkaline medium at temperatures of approximately 20° C. to approximately 160° C., preferably approximately 80° C. to approximately 110° C., and, if appropriate, converting the resulting 3,4,6-trifluorophthalic acid into the anhydride in a known manner by dehydrating it.

The aqueous-alkaline reaction medium is prepared by dissolving in water the alkali metal hydroxides such as, for example, lithium hydroxide, sodium hydroxide or potassium hydroxide, the alkaline earth metal hydroxides such as, for example, magnesium hydroxide, calcium hydroxide, strontium hydroxide or barium hydroxide, and the corresponding carbonates, hydrogen carbonates or phosphates if this results in solutions which have an alkaline action, as described below. These compounds with an alkaline action are employed in amounts such that the pH of the aqueous reaction medium at the reaction temperature is approximately 7 to approximately 15, preferably approximately 11 to approximately 14.

A deposit of these compounds with an alkaline action, due to the fact that they are sparingly soluble in the reaction medium, is quite acceptable.

The amounts of zinc employed are between approximately 100 and approximately 500 mol %, preferably between approximately 200 and approximately 300 mol %, based on tetrafluorophthalic anhydride or tetrafluorophthalic acid.

The conversion of the 3,4,6-trifluorophthalic acid, which has been obtained according to the process, into the anhydride can be effected either by dehydrating a melt of 3,4,6-trifluorophthalic acid in vacuo, or analogously to the preparation of the corresponding trichloro compound by azeotropic dehydration in boiling xylene (Lit. see Synlett (1990), 339–340, cited below). As is known from the literature in the case of polyhalogenated phthalic acids, their dehydration is very simple (Delbridge, American Chemical Journal 41, 400–409 (1909); some of these even undergo conversion into the anhydride upon melting. This means that the preparation method for the phthalic acid is virtually also a preparation method for the anhydride. Conversely, the anhydride even undergoes conversion into the phthalic acid when it is introduced into water.

The process according to the invention can be carried out under atmospheric pressure, elevated pressure or reduced pressure.

Even though dehalogenation of tetrachlorophthalic acid by means of zinc dust in aqueous-alkaline medium is known (Neil J. O'Reilly, William S. Derwin, Lawrence B. Fertel, Henry C. Lin, Synlett (1990) 339–340), it was still surprising that fluoro compounds can also be dehalogenated in a similar manner in aqueous-alkaline medium. The reductive defluorination (JP 01,160,944, Nippon Carbide Ind. Co., Inc., 23.6.89) of tetrafluorophthalodinitrile in aqueous-acid solution is known. The high rate of the reaction is caused here by the high reduction potential of zinc in acid solution. It is known that the reactivity in the dehalogenation follows the sequence F<<Cl<Br<I (cf. Houben-Weyl, Methoden der organischen Chemie, [Methods in Organic Chemistry], Volume IV/1c, pages 364–370). It was furthermore surprising that the reaction is highly selective in removing a fluorine atom in the 4-position to the carboxyl group, as could be demonstrated by $^1$H and $^{19}$F NMR spectroscopy. This selectivity was no longer expected because all fluorine atoms were highly activated by the presence of 6 strongly electron-attracting substituents. There was furthermore a danger of an aromatic nucleophilic substitution of fluorine by hydroxide, but, surprisingly, this was not the case, or only on a very small scale.

The example which follows illustrates the invention in greater detail without imposing any restrictions on it.

EXAMPLE 5.5 g (25 mmol) of tetrafluorophthalic anhydride were added under nitrogen to a solution of 3.58 g (89.5 mmol) of sodium hydroxide in 30 g of water. The mixture was then heated at 100° C., and 6.54 g (0.1 mol) of zinc dust were added. The course of the reaction was monitored by GC(TLC), and the reaction was complete after 12 hours. 50 ml portions of water and ethyl acetate were added and the voluminous solids were filtered off with suction and washed four times with 50 ml portions of water. The colorless filtrate was brought to a pH of 1 and extracted using ethyl acetate. Drying of the organic phases over MgSO$_4$, filtration and removal of the solvent in vacuo gave 4.72 g (22.2 mmol; 89%) of colorless powder which could be identified as 3,4,6-trifluorophthalic acid (melting point 156°–160° C). Azeotropic dehydration in boiling xylene gave 3,4,6-trifluorophthalic anhydride.

3,4,6-Trifluorophthalic acid:

$^{19}$F NMR (DMSO-d$_6$, CFCl$_3$):

$\delta = -113.4$ (B, F-6) (ddd, 1F, $J_{AB}=9.7$ Hz, $J_{BC}=6.9$ Hz, $J_{BD}=15.2$ Hz)

$\delta = -128.6$ (C, F-4) (ddd, 1F, $J_{AC}=10.3$ Hz, $J_{BC}=6.9$ Hz, $J_{CD}=22.9$ Hz)

$\delta = -143.6$ (D, F-3) (ddd, 1F, $J_{AD}=6.4$ Hz, $J_{BD}=15.2$ Hz, $J_{CD}=22.9$ Hz)

$^1$H NMR (DMSO-d$_6$, TMS):

$\delta = 7.80$ (A, H-5) (ddd, 1H, $J_{AB}=9.7$ Hz, $J_{AC}=10.3$ Hz, $J_{AD}=6.4$ Hz)

MS: m/z[%]=55 (2.0), 61 (8.1), 80 (24.5), 99 (12.1), 111 (3.2), 130 (100), 158 (60.3), 202 ((M—H$_2$O)$^+$, 32.2)

If, instead of 3.58 g (89.5 mmol) of sodium hydroxide,

| | |
|---|---|
| 15.21 g (40 mmol) | of sodium phosphate trihydrate, |
| 16.80 g (200 mmol) | of sodium hydrogen carbonate, |
| 5.02 g (89.5 mmol) | of potassium hydroxide, |
| 13.82 g (0.1 mol) | of potassium carbonate, |
| 3.76 g (89.5 mmol) | of lithium hydroxide hydrate, |
| 8.89 g (0.12 mol) | of calcium hydroxide, |
| 15.01 g (0.15 mol) | of calcium carbonate, |
| 16.33 g (0.12 mol) | of calcium hydrogen phosphate dihydrate, |
| 7.57 g (40 mmol) | of barium hydroxide hydrate, or |
| 14.57 g (30 mmol) | magnesium hydroxide carbonate pentahydrate | are used and the procedure is otherwise as described above, then the same result is obtained.

We claim:

1. A process for the preparation of 3,4,6-trifluorophthalic acid of the formula (1)

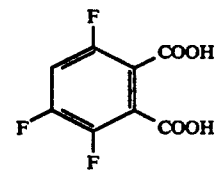

or of the anhydride thereof, which comprises dehalogenating tetrafluorophthalic anhydride of the formula (2)

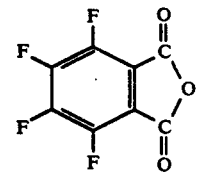

or tetrafluorophthalic acid using zinc in aqueous-alkaline medium at temperatures of approximately 20° C. to approximately 160° C. and, optionally, converting the resulting 3,4,6-trifluorophthalic acid into the anhydride by dehydrating it.

2. The process as claimed in claim 1, wherein the dehalogenation is carried out at temperatures of approximately 80° C. to approximately 110° C.

3. The process as claimed in claim 1, wherein hydroxides, carbonates, hydrogen carbonates or phosphates of alkali metals or alkaline earth metals are included in the aqueous-alkaline reaction medium.

4. The process as claimed in claim 3, wherein the hydroxides, carbonates, hydrogen carbonates or phosphates of alkali metals or alkaline earth metals are employed in amounts such that the pH in the aqueous reaction medium is approximately 7 to approximately 15.

5. The process as claimed in claim 3, wherein the hydroxides, carbonates, hydrogen carbonates or phosphates of alkali metals or alkaline earth metals are employed in amounts such that the pH of the aqueous reaction medium is approximately 11 to approximately 14.

6. The process as claimed in claim 1, wherein approximately 100 to approximately 500 mol % of zinc, based on tetrafluorophthalic anhydride or tetrafluorophthalic acid, are employed.

7. The process as claimed in claim 1, wherein approximately 200 to approximately 300 mol % of zinc, based on tetrafluorophthalic anhydride or tetrafluorophthalic acid, are employed.

8. The process as claimed in claim 1, wherein the dehalogenation is carried out under atmospheric pressure, elevated pressure or reduced pressure.

* * * * *